United States Patent
Musco et al.

(10) Patent No.: US 10,925,916 B2
(45) Date of Patent: Feb. 23, 2021

(54) OLIVE LEAF POWDER (OLP) STRIPS

(71) Applicant: OLYXIR LLC, Livermore, CA (US)

(72) Inventors: Josephine Musco, Livermore, CA (US); James Rossman, Tampa, FL (US); Richard Fielder, Tampa, FL (US)

(73) Assignee: OLYXIR LLC, Livermore, CA (US)

( * ) Notice: Subject to any disclaimer, the term of this patent is extended or adjusted under 35 U.S.C. 154(b) by 5 days.

(21) Appl. No.: 15/776,735

(22) PCT Filed: Jul. 24, 2017

(86) PCT No.: PCT/US2017/043545
§ 371 (c)(1),
(2) Date: May 16, 2018

(87) PCT Pub. No.: WO2018/022516
PCT Pub. Date: Feb. 1, 2018

(65) Prior Publication Data
US 2020/0054703 A1    Feb. 20, 2020

Related U.S. Application Data

(60) Provisional application No. 62/366,418, filed on Jul. 25, 2016.

(51) Int. Cl.
| | | |
|---|---|---|
| *A61K 36/00* | (2006.01) | |
| *A61K 36/63* | (2006.01) | |
| *A61K 9/00* | (2006.01) | |
| *A61K 9/70* | (2006.01) | |

(52) U.S. Cl.
CPC .......... *A61K 36/63* (2013.01); *A61K 9/0056* (2013.01); *A61K 9/7007* (2013.01)

(58) Field of Classification Search
None
See application file for complete search history.

(56) References Cited

U.S. PATENT DOCUMENTS

| | | |
|---|---|---|
| 8,518,435 B2 | 8/2013 | Barron |
| 2004/0247646 A1 | 12/2004 | Ivory |
| 2006/0039953 A1 | 2/2006 | Leung |
| 2008/0081071 A1 | 4/2008 | Sanghvi |

FOREIGN PATENT DOCUMENTS

KR    2011007508 A  *  1/2011

OTHER PUBLICATIONS

International Search rpeort in PCT/US2017/43545, dated Oct. 10, 2017, 1 page.

* cited by examiner

*Primary Examiner* — Qiuwen Mi
(74) *Attorney, Agent, or Firm* — Kilpatrick Townsend & Stockton LLP

(57) ABSTRACT

The present invention is directed to films made with edible polymers and containing a portion of finely ground olive leaf powder (OLP) suitable for preparing a hot or cold beverage and delivering an unexpectedly powerful quantity of natural anti-oxidant in the form of polyphenols.

3 Claims, No Drawings

OLIVE LEAF POWDER (OLP) STRIPS

CROSS-REFERENCES TO RELATED APPLICATIONS

The present invention claims benefit of priority to U.S. Provisional Application No. 62/366,418, filed Jul. 25, 2017, which is incorporated by reference for all purposes.

BRIEF SUMMARY OF THE INVENTION

The present invention is directed to films made with edible polymers and containing a portion of finely ground olive leaf powder (OLP) suitable for preparing a hot or cold beverage and delivering an unexpectedly powerful quantity of natural anti-oxidant in the form of polyphenols.

The invention provides edible, water-soluble film comprising olive leaf powder (OLP) and methods of preparing them. The methods comprise providing a film forming solution comprising a polymer, a humectant, a stabilizer, a surfactant, a flavoring or sweetener, and OLP spreading the solution uniformly on a carrier substrate; and drying the solution thereby forming the water-soluble film.

A number of components can be used to prepare the films of the invention. The polymer can be selected from the group consisting of pullulan, HPMC (hydroxypropyl methyl cellulose), pectin, sodium alginate, starch, Gum Arabic, and CMC (carboxymethyl cellulose). The humectant can be selected from the group consisting of glycerine, propylene glycol, polyethylene glycol, and sorbitol. The stabilizer can be selected from the group consisting of cellulose, oat fiber, and tapioca fiber. The surfactant can be polysorbate 80. The flavoring or sweetener can be selected from the group consisting of sucralose, stevia, and sugar.

The film may comprise the polymer at 10-50% by weight, the humectant at 2-20% by weight, the stabilizer at 10-30% by weight, the surfactant at 1-2% by weight, the flavoring or sweetener at 1-15% by weight, and the OLP at 5-49% by weight. In one embodiment, the film comprises pullulan at 24% by weight, glycerin at 10% by weight, cellulose at 20% by weight. OLP at 35% by weight, polysorbate 80 at 1% by weight, flavoring at 5% by weight, and moisture at 5% by weight.

DETAILED DESCRIPTION OF THE INVENTION

The present invention is directed to a film containing from 10 to 49% by weight of finely ground leaves from an olive tree—referred to as Olive Leaf Powder (OLP). Specific types of olive leaves are selected for their high polyphenol content. The leaves are processed to carefully protect the polyphenols and to permit the grinding of the olive leaves into a fine powder suitable for use in a beverage (see e.g., US 2016/0106128, which is incorporated herein by reference). The OLP is formulated with film forming, edible polymers and other suitable ingredients and is converted into a thin, rapidly soluble film which is comprised of up to 49% OLP by weight. A portion of the OLP film can be placed in a cup of either hot water or cold water where it will instantly dissolve to form a nutritious beverage with a beneficial level of anti-oxidant in the form of polyphenols.

Other functional herbs containing high concentrations of polyphenols and other anti-inflammatory ingredients can be processed in a similar manner and converted into thin films. These films can be cut to a suitable size and weight and can then be added to hot or cold water to form nutritious beverages. Herbs such as hibiscus or dandelion are examples of materials that can be used.

In one aspect, the OLP film is formed without added flavor, sweetener or other modifiers. When a portion of the OLP film is placed in a container of either hot or cold water, it delivers a nutritious beverage with the well-known, robust, natural olive leaf flavor. The use of small amounts of citric acid, or of similar food grade acids, have proven beneficial in delaying or preventing the onset of browning, in the OLP films and in the prepared beverages.

In another aspect, the OLP film is flavored with natural or synthetic flavor ingredients which will enhance the olive leaf flavor without diminishing the health benefits of the beverage. Flavor combinations include, for example:

Honey, Rose, Lemon

Ginger, Peach

Chocolate, Mint

In another aspect, the film can be printed with edible inks to provide a decorative appearance, branding information or instructions for use.

The films can be packaged in cut shapes or rolls or other convenient form for subsequent use by the end user. The films are packaged to maintain freshness and to preserve the desired equilibrium moisture in the film—for example, in moisture barrier bags or other containers. Most conveniently, the OLP films are cut to a size of 2 inches by 3.5 inches with a piece weight of 800 mg (0.8 grams) and multiple pieces of film are stored in a small dispenser pack that can be carried by the end user. One piece of OLP film can be added to approximately 400 ml of water to instantly form a beverage.

The films are useful as a very convenient way to prepare a hot beverage, one cup at a time, while preserving freshness and without incurring waste in the form of excess beverage powder or of excess packaging materials.

This invention also encompasses methods of making the OLP films and preparing them for use by consumers. A particular advantage of the films of the invention is that they provide specific properties of thinness, strength for manufacturing and handling, compact size for ease of packaging, carrying and dispensing the film and instant solubility in water when compared to loose powders, tea bags and other conventional forms of beverage ingredients.

Another advantage of the films is that they help satisfy the important need for increased consumption by consumers of powerful polyphenols (anti-oxidants) by providing a rapid, convenient and economic delivery system. The invention can provide an important tool to increase the consumer's intake of anti-oxidants with their well-documented health benefits.

Examples can be provided showing a number of different formulations as well as the method of preparing the solution, the casting of a uniform wet films, drying the film, removing the film and cutting it to a suitable size for subsequent use in forming a beverage. Data on the size of the film portion, strip weight, solubility performance and other properties can be provided for each example.

Method of Making Film Compositions

The edible, water-soluble films of the invention are formed by processes conventional in the arts, e.g. the paper-making and/or film making industries. For example, the components of the film are conveniently blended in a mixing tank until a homogeneous mixture is achieved. The films can be cast to a desired thickness, on an appropriate substrate, such Mylar, release paper and the like. The films are then dried, for example, in a forced-air oven. The temperature of the drying air and length of drying time depend on the nature of the film as is recognized in the art. The drying temperature can be between about 25° C. and 140° C., in another embodiment from about 60° C. to 90° C. for a duration of about 20 minutes to about 60 minutes, usually from about 30 to about 40 minutes. After exiting from the dryer section of the casting belt, the film can be wound on a spool for storage under sanitary conditions. The film can be cut to form strips of any desired dimension and then stacked and subsequently individually packaged.

The films herein are generally between about 1 and about 10 mils (about 0.025 mm to about 0.25 mm), usually from about 1.2 to about 2.5 mils (about 0.03 mm to about 0.063 mm) thick. The films are usually about 0.75 to about 1 inch wide. The film can be produced in any length.

Exemplary Formulation (by Weight)

| Ingredient | Range, % | Preferred, % |
|---|---|---|
| Pullulan | 20-30 | 24 |
| Glycerin | 10-20 | 10 |
| Cellulose | 10-30 | 20 |
| OLP | 5-49 | 35 |
| Polysorbate 80 | 1-2 | 1 |
| Flavors | 2-15 | 5 |
| Moisture | 3-8 | 5 |
| TOTAL | | 100% |

Preparation of OLP

IR blanching can be done with less energy requirements and without the need of steam or water, allowing water and energy savings during the blanching and drying processes.

| Process | Infrared Blanching |
|---|---|
| Lead Time | 1:15 minutes IR heating on trays (2806 cm$^2$) with 0.392 kg/m$^2$ load density in manual IR system (3.3 kg leaves/h) and 0.216 kg/m$^2$ in IR mobile unit (36 kg/h in a heating section of 90 × 60"). |
| Labor | Half hour needed to blanch 20 kg of olive leaves with one person if using and automatic feeding into the IR mobile unit. |
| Machinery | IR mobile unit. |
| Conditions | 1.5 inch water column gas pressure, 100% propane flow (3.37 kg/h for 161,804 BTL/h). Mean and standard deviation of surface temperatures of IR emitters, Teflon belt and olive leaves are 693.4 ± 101.5, 484.5 ± 52.3, and 257.9 ± 13.8° F., respectively. Residence time of leaves inside the IR heating zone at 4.5 μm IR wavelength is 1 minute and 10 seconds at 42 Hz belt frequency for the IR mobile unit. |
| Limitations | Uniform blanching achieved when leaves overlapping and excess surface water is reduced. |

Hot Air Drying

Four trays of the cabinet dryer hold 880-900 g of blanched olive leaves. Drying was done in 35 minutes at 80° C. Assuming 10 minutes for loading and unloading trays, in an 8 h shift it is possible to do 10 drying batches. Using one drying cabinet in the Pilot Plant we can process 7 kg of fresh leaves/day (approximately 10 kg/day of olive branches considering leaves separation, sorting and waste)

| Process | Hot-air Drying |
|---|---|
| Lead Time | 35-40 minutes in cross-flow hot air at 80° C. in perforated trays |
| Labor | One person to load and unload drying trays |
| Machinery | Proctor & Schwartz Mod. 062 food cabinet dryer heated with steam. The dryer set for 80° C. (176° F.). These cabinet driers are also available to use natural gas for heating the air instead of steam that requires an additional boiler for steam production. |
| Conditions | Four trays (75.5 × 50 cm = 3775 cm$^2$) with 0.0588 g/cm$^2$ load density. 0.456 Kg of dried olive leaves/Kg of fresh olive leaves. Final moisture: 2.9%. Ratio Fresh:Dry = 1.8; Ratio Dry:Fresh = 0.558 |
| Limitations | 2 kg of blanched olive leaves per drying batch (30 Kg blanched olive leaves/shift and 10 Kg of dried olive leaves/shift) with one cabinet dryer. |

Milling

Milling of dried olive leaves have been done with 500, 300, 250 and 200 microns screens, provided a pre-grinding step is performed. No noticeable overheating was observed during milling. Reducing the particle size of the powders from 500 to 200 microns helped to increase solubility and homogeneity of tea solutions.

| Process | Dried Leaf Milling |
|---|---|
| Lead Time | 6 kg of dried leaves/h |
| Labor | One person to load and unload the mill |
| Machinery | SR 300 Retch mill with a GM 300 pre-mill (30 kg/h max capacity). |
| Conditions | Powder is obtained with particle size <200 microns without overheating |
| Limitations | 48 kg of dried milled powder can be obtained per daily labor shift |

Comparison of total soluble phenolics and antioxidant capacity of olive leaf powders with different blanching and drying processes against a commercial olive leaf powder. Infrared blanching and hot-air drying resulted in significantly higher total soluble phenolics and antioxidant capacity in final powders than any other processing method, including infrared blanching and freeze drying.

| Sample description | Total soluble phenolics (mg Gallic Acid/g d.w.) | Antioxidant capacity (μg Trolox/g d.w.) |
|---|---|---|
| Infrared blanching, 1.5 min; hot-air dried for 30 min | 28.653 ± 0.722$^f$ | 105,342 ± 2,804$^f$ |
| Steam blanching, 10 min; hot-air dried for 40 min | 23.307 ± 0.456$^c$ | 86,500 ± 1,054$^d$ |
| No blanching; hot-air dried for 50 min | 18.113 ± 0.501$^b$ | 57,946 ± 984$^b$ |
| Infrared blanching, 1.5 min; freeze-dried for 3 days | 26.103 ± 0.231$^e$ | 98,467 ± 3,122$^e$ |
| Steam blanching, 10 min; freeze-dried for 3 days | 21.263 ± 0.869$^d$ | 76,509 ± 383$^c$ |
| No blanching, freeze-dried for 3 days | 17.613 ± 0.155$^b$ | 54,610 ± 799$^b$ |
| Olive leaf tea from Olivus, Inc. | 12.240 ± 0.405$^a$ | 41,825 ± 1,554$^a$ |

What is claimed is:
1. A method for preparing an edible, water-soluble film comprising olive leaf powder (OLP); the method comprising:

providing a film forming solution comprising a polymer, a humectant, a stabilizer, a surfactant, a flavoring or sweetener, and OLP;

spreading the solution uniformly on a carrier substrate; and drying the solution thereby forming the water-soluble film, wherein:

the polymer is selected from the group consisting of pullulan, HPMC (hydroxypropyl methyl cellulose), pectin, sodium alginate, starch, Gum Arabic, and CMC (carboxymethyl cellulose);

the humectant is selected from the group consisting of glycerine, propylene glycol, polyethylene glycol, and sorbitol;

the stabilizer is selected from the group consisting of cellulose, oat fiber, and tapioca fiber;

the surfactant is polysorbate 80; and the flavoring or sweetener is selected from the group consisting of sucralose, *stevia*, and sugar.

2. The method of claim 1, wherein the film forming solution comprises the polymer at 10-50% by weight, the humectant at 2-20% by weight, the stabilizer at 10-30% by weight, the surfactant at 1-2% by weight, the flavoring or sweetener at 1-15% by weight, and the OLP at 5-49% by weight.

3. The method of claim 1, wherein the film forming solution comprises: pullulan at 24% by weight, glycerin at 10% by weight, cellulose at 20% by weight, OLP at 35% by weight, polysorbate 80 at 1% by weight, flavoring at 5% by weight, and moisture at 5% by weight.

* * * * *